United States Patent
Khudyakov et al.

(10) Patent No.: US 9,891,225 B2
(45) Date of Patent: Feb. 13, 2018

(54) COMPOSITIONS AND METHODS FOR SIMULTANEOUS DETECTION OF HCV ANTIGEN/ANTIBODY

(71) Applicant: The United States of America, as represented by the Secretary, Department of Health and Human Services, Washington, DC (US)

(72) Inventors: Yury E. Khudyakov, Atlanta, GA (US); Anna Obriadina, Nizhni Novgorod (RU)

(73) Assignee: THE UNITED STATES OF AMERICA, AS REPRESENTED BY THE SECRETARY, DEPARTMENT OF HEALTH AND HUMAN SERVICES, Washington, DC (US)

(*) Notice: Subject to any disclaimer, the term of this patent is extended or adjusted under 35 U.S.C. 154(b) by 0 days.

(21) Appl. No.: 14/890,299

(22) PCT Filed: May 12, 2014

(86) PCT No.: PCT/US2014/037648
§ 371 (c)(1),
(2) Date: Nov. 10, 2015

(87) PCT Pub. No.: WO2014/183109
PCT Pub. Date: Nov. 13, 2014

(65) Prior Publication Data
US 2016/0109451 A1    Apr. 21, 2016

Related U.S. Application Data

(60) Provisional application No. 61/821,953, filed on May 10, 2013.

(51) Int. Cl.
| | | |
|---|---|---|
| *C12N 7/00* | (2006.01) | |
| *G01N 33/576* | (2006.01) | |
| *C07K 14/005* | (2006.01) | |

(52) U.S. Cl.
CPC ....... *G01N 33/5767* (2013.01); *C07K 14/005* (2013.01); *C12N 7/00* (2013.01); *C12N 2770/24222* (2013.01); *C12N 2770/24231* (2013.01); *G01N 2333/186* (2013.01); *G01N 2469/20* (2013.01)

(58) Field of Classification Search
None
See application file for complete search history.

(56) References Cited

U.S. PATENT DOCUMENTS

| | | | | |
|---|---|---|---|---|
| 5,574,132 A | * | 11/1996 | Lacroix | C07K 16/109 530/323 |
| 5,627,026 A | | 5/1997 | O'Connor et al. | |
| 6,667,387 B1 | * | 12/2003 | De Leys | C07K 1/13 435/7.1 |
| 7,316,905 B1 | | 1/2008 | Aoyagi et al. | |
| 7,456,257 B2 | * | 11/2008 | Jones | A61K 38/212 530/351 |
| 2012/0230947 A1 | | 9/2012 | Schellenberger et al. | |

OTHER PUBLICATIONS

Sallberg et al. Locations of antibody binding sites within conserved regions of the hepatitis C virus core protein. J Med Virol. May 1994;43(1):62-8.*
GenBank: AB719482.1. Hepatitis C virus subtype 1b gene for core protein, partial cds, isolate: HCC-31. 2012.*
Lin et al., "Design of Novel Conformational and Genotype-Specific Antigens for Improving Sensitivity of Immunoassays for Hepatitis C Virus-Specific Antibodies," *Journal of Clinical Microbiology*, Aug. 2005, vol. 43, No. 8, p. 3917-3924.
Sickinger et al., "Multicenter Evauation of a New, Automated Enzyme-Linked Immunoassay for Detection of Human Immunodeficiency Virus-Specific Antibodies and Antigen," *Journal of Clinical Microbiology*, Jan. 2004, vol. 42, No. 1, p. 21-29.
Speers et al., "Combination Assay Detecting both Human Immunodeficiency Virus (HIV) p24 Antigen and Anti-HIV Antibodies Opens a Second Diagnostic Window," *Journal of Microbiology*, Oct. 2005, vol. 43, No. 10, p. 5397-5399.
El-Shamy et al., "Polymorphisms of Core Protein, NS3-Serine Protease domain and NS5A of RTHepatitis C Virus Genotype 1b Associate with Hepatocellular Carcinoma Development", XP002728833, Database accession No. L0N259 abstract, Mar. 6, 2013.
Steinbrueckner et al., XP002728834, Database accession No. B0FLE4 abstract, Feb. 26, 2008.

* cited by examiner

*Primary Examiner* — Michelle S Horning
(74) *Attorney, Agent, or Firm* — Kilpatrick Townsend & Stockton LLP

(57) ABSTRACT

Compositions and processes are provided for the robust detection of hepatitis C virus in a sample. Compositions include amino acid sequences of HCV core region including or exclusive to residues 14-31 or 50-90 of the HCV core protein. Also provided are processes of detecting HCV in a sample whereby the provided peptides are optionally used alone or in conjunction with antibodies that do not recognize the peptides so that detection is independent of seroconversion in a subject. Using the compositions and processes, HCV can be detected in a sample prior to or following seroconversion leading to robust HCV detection and diagnosis.

15 Claims, No Drawings

SEQUENCE LISTING

```
<160> NUMBER OF SEQ ID NOS: 4

<210> SEQ ID NO 1
<211> LENGTH: 120
<212> TYPE: PRT
<213> ORGANISM: Artificial Sequence
<220> FEATURE:
<223> OTHER INFORMATION: HCV core protein sequence Accession No:
      AB719482.1

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30
```

```
Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
         50                  55                  60

Ile Pro Lys Ala Arg Gln Pro Glu Gly Arg Ala Trp Ala Gln Pro Gly
 65              70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly
            115                 120

<210> SEQ ID NO 2
<211> LENGTH: 18
<212> TYPE: PRT
<213> ORGANISM: Artificial Sequence
<220> FEATURE:
<223> OTHER INFORMATION: protein synthetic sequence

<400> SEQUENCE: 2

Asn Thr Asn Arg Arg Pro Gln Asp Val Lys Phe Pro Gly Gly Gly Gln
 1               5                  10                  15

Ile Val

<210> SEQ ID NO 3
<211> LENGTH: 42
<212> TYPE: PRT
<213> ORGANISM: Artificial Sequence
<220> FEATURE:
<223> OTHER INFORMATION: protein synthetic sequence

<400> SEQUENCE: 3

Arg Lys Thr Ser Glu Arg Ser Gln Pro Arg Gly Arg Arg Gln Pro Ile
 1               5                  10                  15

Pro Lys Ala Arg Gln Pro Glu Gly Arg Ala Trp Ala Gln Pro Gly Tyr
                20                  25                  30

Pro Trp Pro Leu Tyr Gly Asn Glu Gly Leu
            35                  40

<210> SEQ ID NO 4
<211> LENGTH: 10
<212> TYPE: PRT
<213> ORGANISM: Artificial Sequence
<220> FEATURE:
<223> OTHER INFORMATION: protein synthetic sequence

<400> SEQUENCE: 4

Ser Gly Gly Gly Gly Ser Gly Gly Gly Ser
 1               5                  10
```

COMPOSITIONS AND METHODS FOR SIMULTANEOUS DETECTION OF HCV ANTIGEN/ANTIBODY

CROSS REFERENCE TO RELATED APPLICATIONS

This application is the U.S. National Phase of International Patent Application Serial No. PCT/US2014/037648, filed May 12, 2014, which claims priority to U.S. Provisional Patent Application Ser. No. 61/821,953, filed May 10, 2013, the entire contents of which are incorporated herein by reference.

GOVERNMENT INTEREST

The invention described herein may be manufactured, used, and licensed by or for the United States Government.

FIELD OF THE INVENTION

The invention relates generally to disease diagnostics, and in particular to methods for detecting the presence or absence of hepatitis C virus (HCV) in a biological sample or for diagnosing, treating, or preventing HCV infection in a patient.

BACKGROUND OF THE INVENTION

Hepatitis C virus (HCV) represents the major etiologic agent of blood-borne and sporadic non-A, non-B hepatitis. The link between HCV chronic infections with liver cirrhosis and hepatocellular carcinoma makes HCV a significant world-wide health problem.

Two basic tests for HCV are predominantly used for diagnosis of HCV infection: 1) PCR based assays; and 2) serological detection of antibodies. Serological testing for HCV antibodies (Ab) represents the standard method for the detection of HCV infection in a human subject. Early serological assays, however, suffered from significant drawbacks in poor sensitivity thereby producing unacceptably high false negative results. Although the sensitivity and specificity of the second and third generation enzyme immunoassays were significantly improved, the existence of a "window period" from initiation of HCV infection to seroconversion generates an opportunity for false negative results. This period varies from 2 months in immunocompetent subjects to 6-12 months in immunodeficient patients.

HCV has a single strand positive sense RNA genome of approximately 9,400 nucleotides in length. HCV infections, therefore, are also detectable using nucleic acid-based technologies based on the polymerase chain reaction (PCR). In addition to PCR based screening, the combination of PCR screening with serological testing has been proposed. This combination approach decreases the risk of HCV transmission from infected donors during the "window period" due to the PCR approach being capable of detection prior to seroconversion. Unfortunately, genetic testing presents considerable challenges to public health and clinical laboratories owing to requirements for specific equipment and sensitivity to cross-contamination.

As such, there exists a need for compositions and methods that can be used as aids in screening for identification and development of HCV infection a subject.

SUMMARY OF THE INVENTION

Detection of HCV in a biological sample is often confounded by the state of infection in the sample source. For example, it takes several weeks for a subject infected with HCV to seroconvert to a point were anti-HCV antibodies are detectable in the sample. This leaves a window of possible transmission from an infected subject that does not know that they are infected due to the inability of existing assays to detect the presence of the virus. While PCR based assays may detect viral antigen prior to seroconversion, many health centers do not have the resources to perform such assays. Moreover, PCR based assays are susceptible to cross-contamination due their high sensitivity. As such, it is an object of the invention to provide a composition that can be effectively used in an assay to detect the presence of HCV both prior to and following seroconversion and does not rely on PCR based techniques.

An HCV detection agent for the detection of an antibody directed to the HCV core protein in a sample is provided including a peptide comprising 5 or more contiguous amino acids including or between residues 14-31, 50-91, or both of SEQ ID NO: 1, said detection agent excluding residues 41-50 and 100-120 of SEQ ID NO: 1. In some embodiments, the detection agent comprises the sequence of SEQ ID NO: 2. Optionally, the detection agent comprises the sequence of SEQ ID NO: 3. In some embodiments, the amino acid sequence comprises the sequence of SEQ ID NO: 2 and SEQ ID NO: 3, optionally linked directly together or separated by a linker. A linker optionally includes the sequence of SEQ ID NO: 4.

Also provided are processes of detecting the presence or absence of HCV in a biological sample that is useful both before and following seroconversion. As such, the process may be used independent of when a subject was infected with HCV or their ability to produce antibodies to HCV. A process optionally includes contacting a biological sample with the detection agent such as any of the detection agents described or claimed herein; and detecting the presence or absence of an anti-HCV core protein antibody in the biological sample that specifically binds to said detection agent, wherein the detection of the antibody indicates the presence of HCV in said sample. Optionally, the detection of the antibody is used to diagnose the presence or absence of HCV infection in a subject. In some embodiments, the process also includes contacting the sample with an anti-HCV core protein antibody, where the antibody does not bind to the detection agent with sufficient affinity to produce a false negative in the assay. An anti-HCV core protein antibody is optionally monoclonal or polyclonal. Optionally, an anti-HCV core protein antibody and the detection agent are contacting the sample simultaneously. A biological sample is optionally blood, plasma, or serum. A biological sample is optionally a cell or cell extract.

Also provided are kits useful for inclusion in processes to detect the presence or absence of HCV core protein in a biological sample. A kit optionally includes an detection agent including a peptide comprising 5 or more contiguous amino acids including or between residues 14-31, 50-91, or both of SEQ ID NO: 1, said detection agent excluding residues 41-50 and 100-120 of SEQ ID NO: 1. In some embodiments, the detection agent comprises the sequence of SEQ ID NO: 2. Optionally, the detection agent comprises the sequence of SEQ ID NO: 3. In some embodiments, the amino acid sequence comprises the sequence of SEQ ID NO: 2 and SEQ ID NO: 3, optionally linked directly together or separated by a linker. A linker optionally includes the sequence of SEQ ID NO: 4. A kit optionally includes a pharmaceutically acceptable carrier, optionally water or an aqueous buffer.

The compositions and processes of the invention address the long felt need for a rapid, reliable, robust, and inexpensive system for detecting HCV infection in a subject independent of the seroconversion status of the subject.

DETAILED DESCRIPTION OF EMBODIMENTS OF THE INVENTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process is described as an order of individual steps or using specific materials, it is appreciated that described steps or materials may be interchangeable such that the description of the invention includes multiple parts or steps arranged in many ways as is readily appreciated by one of skill in the art.

Viral particles with the physiochemical, morphological and antigenic properties of non-enveloped HCV nucleocapsids are present in the plasma of HCV-infected individuals. These particles have a buoyant density of 1.32-34 g/ml in CsCl, are heterogeneous in size, and express surface epitopes of the HCV core protein located. HCV core plays a vital role in the viral genome encapsidation. It is synthesized only in hepatocytes replicating HCV RNA and as such can serve as a marker of active HCV infection instead of PCR. Core protein is conserved among HCV genotypes. The detection of core protein is easily achievable in HCV infected patients during the window period.

Unfortunately, detection of core protein alone suffers drawbacks due to seroconversion. When antibodies to the core protein appear in the blood, the titer of free core protein decreases. To circumvent this issue, the inventors provide compositions that allow for simultaneous, single well, detection of molecules that are present prior to seroconversion as well as antibodies that are present following seroconversion. Simultaneous detection of both core protein antigen and antibodies directed to core protein represents the best option for sensitive diagnosis of hepatitis C among blood donors.

Provided are compositions and methods for the detection of HCV in a biological sample. A composition includes a detection agent that is a protein molecule. A detection agent includes a peptide having a sequence representing one or more regions of the HCV core protein as defined in Genbank Accession No. AB719482.1 and SEQ ID NO. 1.

MSTNPKPQRK TKRNTNRRPQ DVKFPGGGQI VGGVYLLPRR GPRLGVRATR KTSERSQPRG RRQPIPKARQ PEGRAWAQPG YPWPLYGNEG LGWAGWLLSP RGSRPSWGPT DPRRRSRNLG (SEQ ID NO: 1).

A detection agent includes a peptide representative of at least one region of the HCV core protein. A region of an HCV core protein encompasses 4 or more amino acids, optionally 5 or more amino acids, including or between residues 14-31, 50-91, or both of SEQ ID NO: 1. Optionally, a detection agent includes 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 amino acids. Optionally, a detection agent includes 70 or fewer amino acids, optionally 69 or fewer amino acids. Optionally, a detection agent includes between 4 and 41, optionally between 4 and 18, optionally between 4 and 70 amino acids. Optionally, a detection agent includes from 5 to 17 amino acids. Optionally, a detection agent includes from 5 to 41 amino acids. The forgoing amino acid lengths are optionally exclusive of a tag, linker, or other amino acid or sequence thereof that does not appreciably alter the ability of the detection agent to function as intended.

It is appreciated that the amino acid sequence of a detection agent in any and all embodiments optionally includes one or more amino acid substitutions, deletions, additions, or modifications to the sequence including or between residues 14-31, 50-91, or both of SEQ ID NO: 1 so long as such a region maintains its function as an epitope for an anti-core protein antibody as generated toward an epitope having a sequence identical to SEQ ID NO: 1, residues 14-31, 50-91, or a relevant portion thereof. Illustratively, detection agent may include one or more amino acid substitutions, deletions, additions, or modifications to the sequence of residues 14-31 or 50-91 that does not destroy the ability of an antibody directed to one or both of these regions, or portions thereof, from binding to the detection agent.

In some embodiments, a detection agent includes a first epitope region. A first epitope region optionally includes 5 or more amino acids of residues 14-31 of SEQ ID NO: 1. A first epitope region optionally includes the sequence of NTNRRPQDVKFPGGGQIV (SEQ ID NO: 2). Optionally, the detection agent includes a second epitope region. A second epitope region optionally includes 5 or more amino acids of residues 50-91 of SEQ ID NO: 1, optionally residues 50-90 of SEQ ID NO: 1 alone or including one additional amino acid at the C-terminus, optionally M or L. Optionally, a second epitope region includes the sequence RKTSERSQPRGRRQPIPKARQPEGRAWAQPGYPW-PLYGNEGL (SEQ ID NO: 3). Optionally, a second epitope region excludes the last L in SEQ ID NO: 3.

A detection agent optionally includes a linker. A linker is optionally positioned between a first epitope region and a second epitope region. A linker is optionally a peptide of 1 or more amino acids wherein the linker does not correspond to a portion of the HCV core protein amino acid sequence. Optionally, a linker includes from 2 to 50 amino acids or any number or range therebetween. Optionally, a linker includes 2, 3, 4, 5, 6, 7, 8, 9, 10, 11, 12, 13, 14, 15, 16, 17, 18, 19, 20, or more amino acids. Optionally a linker includes the sequence of SGGGGSGGGS (SEQ ID NO: 4).

A detection agent optionally excludes one or more contiguous residues of amino acids 1-13, 32-49, 41-49, 41-50, 91-120, or 100-120 of SEQ ID NO: 1, or any combination thereof.

The detection agent includes a peptide, or is entirely a peptide. The terms "peptide," "polypeptide," and "protein" as used herein and are intended to mean a natural or synthetic compound containing 4 or more amino acids. Amino acids that may be present in a peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the "peptide" as used herein may include peptides having between 5 and about 200 amino acids or any value or range therebetween.

Modifications and changes can be made in the sequence of a peptide relative to a wild type sequence of SEQ ID NO: 1 or an epitope region thereof and still obtain a molecule capable of being specifically bound by an anti-core protein antibody. For example, certain amino acids can be substituted for other amino acids in a sequence without appreciable loss of activity, wherein activity is the ability to be specifically bound by an anti-core protein antibody. Because it is the interactive capacity and nature of a peptide that defines that peptide's activity, certain amino acid sequence substitutions can be made in a peptide sequence and nevertheless obtain a polypeptide with like properties.

In making such changes, the hydropathic index of amino acids can be considered. The importance of the hydropathic amino acid index in conferring activity on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 are optional, those within ±1 are optional, and those within ±0.5 are optional.

Substitution of like amino acids can also be made on the basis of hydrophilicity, particularly, where the activity equivalent polypeptide or peptide thereby created is intended. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an activity equivalent or superior peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Such substitutions are typically considered conservative substitutions. Exemplary conservative substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a peptide as set forth above. In particular, embodiments of the polypeptides can include variants having about 50%, 60%, 70%, 80%, 90%, and 95% sequence identity to the polypeptide of interest.

A peptide is obtained by any of various methods known in the art illustratively including isolation from a cell or organism, chemical synthesis, expression of a nucleic acid and partial hydrolysis of proteins. Chemical methods of peptide synthesis are known in the art and include solid phase peptide synthesis and solution phase peptide synthesis for instance. A peptide included in a detection agent may be a naturally occurring or non-naturally occurring peptide. The term "naturally occurring" refers to a peptide endogenous to a cell, tissue or organism and includes allelic variations. A non-naturally occurring peptide is synthetic or produced apart from its naturally associated organism or modified and is not found in an unmodified cell, tissue or organism.

A peptide is illustratively recombinant. An inventive peptide may be co-expressed with associated tags, modifications, other proteins such as in a fusion peptide, or other modifications or combinations recognized in the art. Illustrative tags include 6×His, FLAG, biotin, ubiquitin, SUMO, or other tag known in the art. A tag is illustratively cleavable such as by linking to a peptide via an enzyme cleavage sequence that is cleavable by an enzyme known in the art illustratively including, but not limited to Factor Xa, thrombin, SUMOstar protein as obtainable from Lifesensors, Inc., Malvern, Pa., or trypsin. It is further appreciated that chemical cleavage is similarly operable with an appropriate cleavable linker.

Peptide expression is illustratively accomplished from transcription of nucleic acid sequence encoding a peptide and translation of RNA transcribed from the nucleic acid sequence. Peptide expression is optionally performed in a cell based system such as in *E. coli*, Hela cells, or Chinese hamster ovary cells. It is appreciated that cell-free expression systems are similarly operable.

A detection agent is optionally isolated or purified. The terms "purified" or "isolated" as used herein, are intended to refer to a composition, isolatable from other components, wherein the composition is purified to any degree relative to its naturally-obtainable state or state as expressed in a cell or synthetic system. A purified peptide, therefore, also refers to a peptide, free from the environment in which it may naturally occur.

An isolated peptide may be subjected to fractionation to remove various other components. Where the term "substantially" purified is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure as based on knowledge in the art. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the detection agent always be provided in its most purified state. Indeed, it is contemplated that less substantially purified products will have utility in certain embodiments. Partial purification may be accomplished by using fewer purification steps in combination, or by utilizing different forms of the same general purification scheme. For example, a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the gel migration of a peptide can vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

Isolation of a detection agent is included in some embodiments. Methods of peptide isolation illustratively include column chromatography, affinity chromatography, gel electrophoresis, filtration, or other methods known in the art. In some embodiments, peptide is expressed with a tag operable for affinity purification. A tag is optionally a 6×His tag. A 6×His tagged inventive protein is illustratively purified by Ni-NTA column chromatography or using an anti-6×His tag antibody fused to a solid support. (Geneway Biotech, San Diego, Calif.) Other tags and purification systems are similarly operable.

It is appreciated that a peptide is optionally not tagged. In such embodiments purification is optionally achieved by methods known in the art illustratively including ion-exchange chromatography, affinity chromatography, precipitation with salt such as ammonium sulfate, streptomycin sulfate, or protamine sulfate, reverse phase chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

A detection agent is illustratively recombinant. Protein expression is illustratively accomplished from transcription of a nucleic acid sequence encoding a detection agent, translation of RNA transcribed from the nucleic acid sequence, modifications thereof, or fragments thereof. Protein expression is optionally performed in a cell based system such as in *E. coli*, Hela cells, or Chinese hamster ovary cells. It is appreciated that cell-free expression systems are similarly operable.

A peptide is optionally chemically synthesized. Methods of chemical synthesis have produced proteins greater than 600 amino acids in length with or without the inclusion of modifications such as glycosylation and phosphorylation. Methods of chemical protein and peptide synthesis illustratively include solid phase protein chemical synthesis. Illustrative methods of chemical protein synthesis are reviewed by Miranda, L P, *Peptide Science,* 2000, 55:217-26 and Kochendoerfer G G, *Curr Opin Drug Discov Devel.* 2001; 4(2):205-14.

A detection agent is optionally be characterized by measurements including, without limitation, western blot, macromolecular mass determinations by biophysical determinations, SDS-PAGE/staining, HPLC and the like, antibody recognition assays, cell viability assays, apoptosis assays, and assays to infer immune protection or immune pathology by adoptive transfer of cells, proteins or antibodies.

Also provided are isolated oligonucleotides encoding a detection agent. These oligonucleotides can be used to produce the peptides included in a detection agent. It is appreciated that the degenerate nucleic acid code is well understood such that one of skill in the art fully and immediately understands a nucleic acid sequence that will produce a desired peptide sequence. As such, an oligonucleotide includes any polynucleotide sequence that will encode a detection agent.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof.

Included in this definition are modified nucleotides which include additions to the sugar-phosphate groups as well as to the bases.

The term "oligonucleotide" refers to multiple nucleotides attached in the form of a single or double stranded molecule that can be natural, or derived synthetically, enzymatically, and by cloning methods. The term "oligonucleotide" refers to a polynucleotide of less than 2000 nucleotides.

An oligonucleotide as used herein refers to single- or double-stranded molecules that may be DNA, including of the nucleotide bases A, T, C and G, or RNA, comprised of the bases A, U (substitutes for T), C, and G. The oligonucleotide may represent a coding strand or its complement. Oligonucleotides may be identical in sequence to the sequence naturally occurring or may include alternative codons that encode the same amino acid as that found in the naturally occurring sequence. Furthermore, oligonucleotides may include codons that represent conservative substitutions of amino acids as are well known in the art.

The oligonucleotide encoding the detection agent of this invention can be part of a recombinant nucleic acid construct including any combination of restriction sites and/or functional elements as are well known in the art that facilitate molecular cloning and other recombinant DNA manipulations. Thus, the present invention further provides a recombinant oligonucleotide construct including a nucleic acid encoding a peptide and/or polypeptide of this invention.

The present invention also provides a vector with a nucleic acid sequence encoding peptide sequence therein. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

An inventive oligonucleotide is provided. An oligonucleotide optionally encodes a peptide including a sequence of SEQ ID NO: 2, SEQ ID NO: 3, SEQ ID NO: 4, a combination of SEQ ID NO: 2, SEQ ID NO: 4, and SEQ ID NO: 3 arranged in any order, or in the order listed. The genetic code is a degenerate code whereby specific nucleic acid sequences encode for particular amino acids. As such it is well within the level of those of skill in the art to determine a nucleic acid sequence that will encode the inventive peptides.

The inventive nucleic acid sequence is optionally isolated from the cellular materials with which it is naturally associated. As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression. Methods of oligonucleotide isolation are similarly recognized in the art. Illustratively, plasmid DNA amplified in *E. coli* is cleaved by suitable restriction enzymes such as NdeI and XhoI to linearize DNA. The DNA is subsequently isolated following gel electrophoresis using a S.N.A.P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleotide sequences of the invention may be isolated by conventional uses of polymerase chain reaction or cloning techniques such as those described in conventional texts. For example, the nucleic acid sequences of this invention may be prepared or isolated from DNA using DNA primers and probes and PCR techniques. Alternatively, the inventive nucleic acid sequence may be obtained from gene banks derived from *Bacillus anthracis* whole genomic DNA. These sequences, fragments thereof, modifications thereto and the full-length sequences may be constructed recombinantly using conventional genetic engineering or chemical synthesis techniques or PCR, and the like.

Also provided is a host cell transformed with an appropriate vector or with the inventive peptide sequence. Illustrative host cells include *E. coli* or Sf9 cells. Optionally, cell transfection is achieved by electroporation.

As used herein, the terms "engineered" and "recombinant" cells are synonymous with "host" cells and are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant encoded peptide in accordance with the present invention one would prepare an expression vector that comprises an oligonucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* .chi. 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins. Optionally, the oligonucleotide is included in a pETitN vector for expression in *E. coli*.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and glyceraldehyde-3-phosphate dehydrogenase, and enzymes responsible for maltose and galactose utilization.

In addition to microorganisms, cultures of cells derived from multicellular organisms may also be used as hosts. In principle, any such cell culture is operable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autographica californica* nuclear polyhedrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., U.S. Pat. No. 4,215,051).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the Bgll site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin. It is appreciated that numerous other selection systems are known in the art that are similarly operable in the present invention.

It is contemplated that the isolated oligonucleotides or detection agents may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

An oligonucleotide can be in a cell, which can be a cell expressing the oligonucleotide whereby a detection agent is produced in the cell. In addition, the vector can be in a cell, which can be a cell expressing the oligonucleotide whereby a detection agent is produced in the cell. It is also contemplated that the oligonucleotides and/or vectors can be present in a host animal (e.g., a transgenic animal) that expresses the oligonucleotide and produces the detection agent.

The oligonucleotide encoding the detection agent can be any oligonucleotide that functionally encodes the detection agent. To functionally encode the detection agent (i.e., allow the oligonucleotide to be expressed), the oligonucleotide can include, for example, expression control sequences, such as an origin of replication, a promoter, an enhancer and necessary information processing sites, such as ribosome binding sites, RNA splice sites, polyadenylation sites and transcriptional terminator sequences.

Expression control sequences useful include promoters derived from metallothionine genes, actin genes, immunoglobulin genes, CMV, SV40, adenovirus, bovine papilloma virus, etc. A nucleic acid encoding a selected peptide or polypeptide can readily be determined based upon the genetic code for the amino acid sequence of the selected peptide or polypeptide and many nucleic acids will encode any selected peptide or polypeptide. Modifications in the nucleic acid sequence encoding the detection agent are also contemplated. Modifications that can be useful are modifications to the sequences controlling expression of the detection agent to make production of the detection agent inducible or repressible as controlled by the appropriate inducer or repressor. Such methods are standard in the art. The oligonucleotide can be generated by means standard in the art, such as by recombinant nucleic acid techniques and by synthetic nucleic acid synthesis or in vitro enzymatic synthesis.

Antibodies generated against or binding to regions of the HCV core protein that are not represented by those included in a detection agent are useful as research tools, clinical diagnostic assay components, or other uses. An antibody optionally is used as a screening agent for the presence or absence of HCV core protein in a sample by specifically binding to an epitope within a region of a core protein. An antibody as used in a process or kit of the invention optionally does not specifically or non-specifically bind to a detection agent and is herein termed a detection antibody. Thus, a detection agent and a detection antibody can be used in a single biological sample simultaneously to detect one or both of core protein or antibodies directed to the core protein in the sample.

The terms "antibody" and "antibodies" as used herein include monoclonal, polyclonal, chimeric, single chain, bispecific, simianized, and humanized antibodies, as well as Fab fragments, including the products of an Fab immunoglobulin expression library.

Antibodies as used herein can be polyclonal or monoclonal. An intact antibody, a fragment thereof (e.g., Fab or F(ab')2), or an engineered variant thereof (e.g., sFv) can also be used. Such antibodies can be of any immunoglobulin class including IgG, IgM, IgE, IgA, IgD and any subclass thereof.

The antibodies provided herein can be monoclonal or polyclonal, optionally a F(ab)'$^2$ fragment lacking the Fc portion of the antibody. The antibodies can be prepared by generating B cell hybridomas, or by using laboratory animals such as mouse, humanized mouse, rat, rabbit or goat that are immunized with the a detection agent or peptide epitope portion thereof. The peptides and/or polypeptides optionally contain deletion, insertion and/or substitution mutations. Screening can then be carried out to identify antibodies that specifically bind to a detection agent.

The term "specifically bind" as used herein is intended to mean that an antibody has suitable affinity to the epitope sequence to be used in an immunoassay while having no detectable binding to non-epitope sequences present in a biological sample, illustratively serum.

Monoclonal antibodies are generated by methods well known to those skilled in the art. An illustrative method is a modified version of the method of Kearney et al., *J. Immunol.* 123:1548-1558 (1979). Briefly, animals such as mice or rabbits are inoculated with the immunogen in adjuvant, and spleen cells are harvested and mixed with a myeloma cell line. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce monoclonal antibodies that specifically bind a detection agent. Hybridomas producing antibodies are cloned, expanded and stored frozen for future production.

Techniques for the production of single chain antibodies are known to those skilled in the art and described in U.S. Pat. No. 4,946,778 and can be used to produce single chain antibodies to the motifs described herein. Phage display technology may be used to select antibody genes having binding activities for the peptides of interest.

The antibody is optionally modified so that it is "humanized" by transplanting the complementarity determining regions of the hybridoma-derived antibody into a human monoclonal antibody as described by Jones et al., *Nature,* 32: 1522-525 (1986).

Polyclonal antibodies can be obtained by immunizing donors with vaccines or immunogens. Serum from the selected donors is then pooled and made into immunoglobulin preparations.

An immunogen used to generate an antibody as used in the present invention may optionally be modified to increase its immunogenicity. In a non-limiting example, the immunogen (antigen) may be coupled to chemical compounds or immunogenic carriers, provided that the coupling does not interfere with the desired biological activity of either the antigen or the carrier. For a review of some general considerations in coupling strategies, see Antibodies, A Laboratory Manual, Cold Spring Harbor Laboratory, ed. E. Harlow and D. Lane (1988). Useful immunogenic carriers known in the art, include, without limitation, keyhole limpet hemocyanin (KLH); bovine serum albumin (BSA), ovalbumin, PPD (purified protein derivative of tuberculin); red blood cells; tetanus toxoid; cholera toxoid; agarose beads; activated carbon; or bentonite. Useful chemical compounds for coupling include, without limitation, dinitrophenol groups and arsonilic acid.

The immunogen may also be modified by other techniques illustratively including denaturation with heat and/or SDS.

An immunogen may also be used in the form of a pharmaceutically acceptable salt. Suitable acids and bases which are capable of forming salts with the polypeptides of the present invention are well known to those of skill in the art, and include inorganic and organic acids and bases.

An immunogen optionally includes or consists of the amino acids 1-13, 32-49, or 91 to 120 of SEQ ID NO: 1, or any combination thereof. An immunogen optionally includes any amino acid sequence of HCV core protein with the exception of residues 14-31 or 51-90 of SEQ ID NO: 1. Methods of producing such immunogens are described herein and well known in the art. Illustrative examples of antibodies that do not recognize a detection agent include those described in Barban, V., et al., *J. Gen. Virol.,* 2000; 81:461-469.

In another aspect, a kit is provided that includes a detection agent and a suitable carrier. Suitable pharmaceutically acceptable carriers facilitate use of the peptide in a system or process for the detection of the presence or absence of an antibody that specifically binds the detection agent. Carriers may be selected by one of skill in the art. Exemplary carriers include sterile water or saline, an aqueous buffer system such as HEPES, TRIS, or phosphate based buffer system, lactose, sucrose, calcium phosphate, gelatin, dextran, agar, pectin, peanut oil, olive oil, and sesame oil.

Optionally, the detection agent or detection antibody may be combined with conventional pharmaceutical ingredients, such as preservatives, or chemical stabilizers. Suitable ingredients operable herein include, for example, casamino acids, sucrose, gelatin, phenol red, N—Z amine, monopotassium diphosphate, lactose, lactalbumin hydrolysate, and dried milk.

Also provided is a process of detecting the presence or absence of HCV in a subject. A process includes contacting a sample with a detection agent and detecting the specific binding of an antibody present in the sample with the detection agent. During periods of HCV infection in which antibodies are present at a sufficient level, antibodies against the core antigen specifically at residues 14-31 or 50-91, will be detectable by their specific binding to a detection agent. It has been discovered that the regions of HCV core protein encompassing a first and second epitope represent unexpectedly important regions for the production of antibodies to HCV core protein. Thus, a detection agent that includes an epitope representing all or a portion of residues 14-31 or 50-91 has utility for the detection of HCV infection in a subject by the presence of anti-core protein antibodies in the subject. As such, a process includes contacting a sample, or portion thereof, with a detection agent to allow specific binding to an anti-core protein antibody. When specific binding is detected, the presence of HCV infection is confirmed. When specific binding is not detected, this indicates either the absence of HCV infection or that the subject has not yet serocoverted and has not yet produced antibodies.

To address the issue of detection prior to seroconversion, a process optionally includes contacting a biological sample with both a detection agent and a detection antibody that does not bind to any region of the detection agent. Thus, the detection agent can be used to detect the presence or absence of antibodies to the core protein, and the detection antibody can be used to detect the presence or absence of core protein either before or after seroconversion. Thus, a robust and complete assay system is provided. Similar assay systems are presented in U.S. Pat. No. 7,316,905, the procedures of which are amenable to use with a detection agent as described herein and a detection antibody. The peptides and antibodies of U.S. Pat. No. 7,316,905 are inoperable in the preset processes, however.

As used herein, the terms "subject" is defined as any organism capable of hosting infection by a virus, illustratively HCV. A subject illustratively includes: any mammal such as humans, non-human primates, horses, goats, cows, sheep, pigs, dogs, cats, rodents; as well as cells. In some embodiments, a subject is a human and excludes other organisms. In some embodiments, a subject is a cell and is exclusive of an organism.

As used herein, the term "biological sample" is defined as a sample obtained from a biological organism, a tissue, cell, cell culture medium, or any medium suitable for mimicking biological conditions, or from the environment. Non-limiting examples include saliva, gingival secretions, cerebrospinal fluid, gastrointestinal fluid, mucous, urogenital secretions, synovial fluid, cerebrospinal fluid, blood, serum, plasma, urine, cystic fluid, lymph fluid, ascites, pleural effusion, interstitial fluid, intracellular fluid, ocular fluids, seminal fluid, mammary secretions, vitreal fluid, nasal secretions, water, air, gas, powder, soil, biological waste, feces, cell culture media, cytoplasm, cell releasate, cell lysate, buffers, or any other fluid or solid media.

A process is optionally used to diagnose infection of a subject by HCV. Optionally, a process is used in the treatment of HCV infection to determine if the virus has been cleared from the subject or if further treatments are needed.

Overall, the detection agents and processes provided represent a robust and complete detection system for the detection of HCV or diagnosis of HCV infection in a subject. The detection agents may be used to provide detection of HCV infection after seroconversion. In some embodiments, a full scope of HCV infection is detectable by combining a detection agent with a detection antibody to detect HCV infection independent of the seroconversion status of the subject thereby eliminating the limited window of many prior diagnostic processes.

Various aspects of the present invention are illustrated by the following non-limiting examples. The examples are for illustrative purposes and are not a limitation on any practice of the present invention. It will be understood that variations and modifications can be made without departing from the spirit and scope of the invention. A person of ordinary skill in the art readily understands where such reagents may be obtained.

EXAMPLES

Example 1: Production of Detection Agent

Assay for the simultaneous detection of Ab's and core requires the application of a recombinant protein that, although is capable of detecting HCV core-specific Ab's, cannot immunoreact with the monospecific Ab's used for the core capture from serum. In some instances, the gene encoding a protein containing HCV core regions 14-31 aa and 50-91 aa separated by a linker with the aa sequence SGGGGSGGGS was constructed and expressed in *E. coli* using the pETitN vector. The N-terminal 6×His tag was added to facilitate purification of the antigen by the Ni-Agarose-affinity chromatography (Invitrogen, USA).

Example 2: Capture and Detection Antibodies

A commercially available monoclonal Ab (Pierce Biotechnology, Rockford, Ill.) is labeled by biotin and used for general detection of HCV core protein. Monospecific polyclonal Ab's are used to capture HCV core. The immunization protocol and development of monospecific polyclonal antibodies are described in Puffinbarger N, Hansen K, Resta R, Laurent A, Knudsen T, Madara J, Thompson L. Production and characterization of multiple antigenic peptide antibodies to the adenosine $A_{2b}$ receptor. Mol. Pharm. 1995; 47:1126-1132. The Ab's were purified by affinity chromatography using synthetic peptides comprising the HCV core regions at positions 1-30 aa and 28-58 aa.

Example 3: Detection of Anti-Core Antibodies or Core Protein in Serum of Subjects Infected by HCV For anti-HCV detection, five recombinant HCV proteins were used: (i) the modified recombinant detection agent of Example 1, (ii) NS3 (aa positions 1356-1459) of HCV genotype 1a, (iii) NS3 (aa positions 1192-1459) of HCV genotype 1b, (iv) a mosaic protein containing immunodominant regions of the NS4 protein (aa positions 1691-1710, 1712-1733, and 1921-1940) of HCV genotypes 1, 2, 3, and 5, and (v) NS5 (aa positions 2061-2302) of HCV genotype 1a. All proteins except for detection agent were expressed in *E. coli* as fusion proteins with glutathione S-transferase (GST) and were purified using affinity chromatography (Pharmacia Biotech, Inc., Piscataway, N.J.).

The detection agents and anti-core antibodies were diluted in phosphate-buffered saline (PBS). Individual wells of Nunc MaxiSorp plates (Nunc, Inc., Denmark) were coated with 100 μl volumes of a mixture containing 1 μg/ml of core protein (detection agent), 1 μg/ml of the genotype 1a NS3 protein, 1 μg/ml of the genotype 1b NS3 protein, 1 μg/ml of the NS4 mosaic protein, 1 μg/ml of the NS5 Ag, and 2 μg/ml of the anti-core antibodies. Plates were incubated overnight at ambient temperature and then blocked with 150 μl/well of 10 mM PBS containing 1% BSA, 5% sucrose for 2 h at room temperature. The blocking solution was aspirated and the plates were dried and packed in foil pouches with desiccant.

Nineteen commercially available seroconversion panels containing serial samples from individual blood donors with HCV infection were obtained from Zeptometrix (Buffalo, N.Y.) and SeraCare Life Sciences, Inc. (Milford, Mass.). All panels were tested by EIA-HCV Ag/Ab.

Anti-HCV-positive serum samples (n=374) were obtained from SeraCare Life Sciences, Inc. and Diagnostic Systems (Nizhniy Novgorod, Russia). Samples from SeraCare were tested by Ortho EIA Anti-HCV 3.0. Sera from Diagnostic Systems were tested by DS-EIA-Anti-HCV (Diagnostic Systems, Nizhniy Novgorod, Russia) and Ortho RIBA HCV 3.0.

Serum samples (n=208) negative for markers of HCV infection were obtained from Innovative Research (Novi, Mich.), Diagnostic Systems (Nizhniy Novgorod, Russia) and SeraCare Life Sciences, Inc. (Milford, Mass.); 23 of them were obtained from hospitals and were negative for markers of HCV infection but positive for some other viral infections. All samples were tested by DS-EIA-Anti-HCV.

The EIA-HCV Ag/Ab assay is a combination of the sandwich format for the detection of HCV core antigen and the indirect format for antibody detection using the detection agent of Example 1. In the first step, conjugate 1 containing biotinylated monoclonal Ab against the HCV core Ag, samples and controls were added to wells and incubated for 30 min at 37° C. with shaking. After washing, streptavidin-peroxidase and conjugate 2 (peroxidase-labelled antibodies to human IgG) were added. Plates were incubated for 30 min at 37° C. with shaking. The unbound conjugate was removed by additional washing step and the antigen-antibody complex was detected by addition of the substrate. After reaction stopping, absorbance intensity was measured at 450 nm A sample was considered positive when its optical density was greater than or equal to the cut-off value.

To calculate the cut-off (CO) value we tested 208 HCV-negative serum specimens by EIA-HCV-Ag/Ab. The mean OD was 0.033, median −0.025. Two methods were used to establish CO. The first method was based on calculating the $99.9^{th}$ percentile of OD values for negative samples. Relative Operating Characteristics (ROC) analysis was used as the second method. The maximum sum of sensitivity and specificity was used to select CO. Both methods produced a similar CO.

All anti-HCV-positive specimens (n=374) were found positive by EIA-HCV Ag/Ab, with 88% of the specimens having the OD/CO values of >9.0. OD/CO varied from 1.2 to 40.0. The mean OD/CO was 22.9 and median was 24.5.

All specimens (n=45) from patients infected with HCV of known genotypes were found positive by EIA-HCV Ag/Ab. There was no difference between the average and median OD/CO for these specimens (Table 1).

TABLE 1

| Genotype | N | Mean OD/CO | Median OD/CO |
|---|---|---|---|
| 1 | 25 | 11.4 | 12.0 |
| 2 | 5 | 10.6 | 12.0 |
| 3 | 15 | 11.3 | 12.0 |

Serial specimens from seroconversion panels (n=19) were tested by EIA-HCV-Ag/Ab to evaluate sensitivity of early HCV detection and compare to other assays. Results are shown in Table 2.

EIA-HCV-Ag/Ab detected HCV infection in 10 panels as early as PCR. In one panel (PHV901), it detected HCV infection earlier than PCR. EIA-HCV-Ag/Ab detected HCV infection in 16 panels as early as the HCV Ag/Ab Combo Abbott-Murex test and earlier in 2 panels. EIA-HCV-Ag/Ab was as sensitive as Monolisa HCV AgAb ULTRA BioRad in 6 out of 11 panels. EIA-HCV-Ag/Ab detected HCV infection earlier than Monolisa HCV AgAb ULTRA BioRad in another 4 out of 11 panels.

The average delay in the detection of seroconversion was determined by comparison to HCV PCR. The results are shown in Tables 3 and 4.

TABLE 3

| Overall delay in detecting seroconversion compared to PCR | Anti-HCV Ortho HCV 3.0 | HCV Ag/Ab Combo Abbott-Murex | Monolisa HCV AgAb ULTRA | EIA-HCV-Ag/Ab |
|---|---|---|---|---|
| Range (days) | 20-65 | 0-53 | 0-32 | −65-32 |
| Mean (days) | 32.3 | 6.2 | 9.5 | −1.6 |
| Median (days) | 28 | 0 | 0 | 0 |

TABLE 4

| Overall delay in detecting seroconversion compared with PCR | HCV Ag/Ab Combo Abbott-Murex | EIA-HCV-Ag/Ab |
|---|---|---|
| Range (days) | −28-53 | −65-32 |
| Mean (days) | 3.1 | 0.2 |
| Median (days) | 0 | 0 |

The coefficients of intra-assay and inter-assay variation were calculated by testing 4 replicates of 3 sera in the same run and 4 replicates of 3 sera in 5 different runs, respectively. Intra- and inter-assay variation were <8%. Data are shown in Table 5.

TABLE 2

| | | | Days to detection from the first available bleed | | | |
|---|---|---|---|---|---|---|
| Panel | Specimens (n) | Genotype* | HCV-PCR* | Anti-HCV Ortho HCV 3.0* | HCV Ag/Ab Combo Abbott-Murex | Monolisa HCV AgAb ULTRA** | DS-EIA-HCV-Ag/Ab |
| 9041 | 8 | ND | 24 | 62 | 24 | 27 | 24 |
| 9044 | 6 | ND | 0 | 25 | 0* | 0 | 0 |
| 9045 | 8 | ND | 0 | 41 | 0* | 0 | 0 |
| 9047 | 10 | ND | 0 | 28 | 0* | 0 | 0 |
| 6212 | 9 | 1 | 0 | 23 | 53* | 23 | 32 |
| 6213 | 8 | ND | 15 | 43 | 30* | 37 | 30 |
| 6214 | 13 | 1 | 0 | 32 | 0* | 25 | 0 |
| 6215 | 4 | 1a | 0 | 20 | 0* | 0 | 0 |
| 6222 | 8 | ND | 17 | 40 | 17* | 17 | 17 |
| PHV901 | 11 | 1a | 65 | 97 | 65** | 97 | 0 |
| PHV917 | 9 | 2b | 20 | 85 | 20** | 20 | 20 |
| 10003 | 13 | 3 | 26 | >51 | 30* | ND | 30 |
| 10008 | 10 | 1a/1b | 9 | >31 | 15* | ND | 15 |
| 10016 | 12 | 2 | 43 | >71 | 47* | ND | 47 |
| 10020 | 13 | 1a | 25 | >57 | 25* | ND | 25 |
| 10021 | 14 | 1a | 35 | >63 | 7* | ND | 37 |
| 10023 | 21 | 1a | 39 | >71 | 42* | ND | 42 |
| 10029 | 16 | 1 | 48 | >71 | 48* | ND | 48 |
| 10051 | 14 | 1b | 36 | >50 | 38* | ND | 38 |

*Data from the seroconversion panels data sheets
**Data from the evaluation of Murex HCV Ag/Ab (MiDAS, 2007)

TABLE 5

| Serum | Intra-assay | | Inter-assay | |
|---|---|---|---|---|
| | Mean OD/CO | CV, % | Mean OD/CO | CV, % |
| A | 7.95 | 1.2 | 8.08 | 4.2 |
| B | 4.46 | 2.6 | 4.39 | 5.4 |
| C | 3.00 | 5.9 | 3.15 | 6.3 |

REFERENCE LIST

Velati C, Romano L, Baruffi L, Pappalettera M, carreri V, Zanetti A. Residual risk of transfusion-transmitted HCV and HIV infections by antibody-screened blood in Italy. Transfusion 2002; 42:989-993

Van der Poel C L, Cuypers H T, Reesink H W. Hepatitis C virus six years on. Lancet 1994; 344: 1475-1479

Puffinbarger N, Hansen K, Resta R, Laurent A, Knudsen T, Madara J, Thompson L. Production and characterization of multiple antigenic peptide antibodies to the adenosine $A_{2b}$ receptor. Mol. Pharm. 1995; 47:1126-1132

Busch M. Closing the windows on viral transmission by blood transfusion. In S. L. Stramer (ed.), Blood safety in the new millennium. American association of blood bunks. 2001; Bethesda, Md.: 33-54

Toyoda H, Sakamoto H, Mizuno T, Horiguchi Y, Nakano H. Eradication of hepatitis C virus 1b by interferon in a health care worker with acute hepatitis following needlestick transmission from a patient with chronic hepatitis C unresponsive to interferon. Scand. J. Gastroenterol. 2000; 35:1117-1120

Sillanpaa M, Melen K, Porka P, Fagerlund R, Nevalainen K, Lappalainen M, Julkunen I. Hepatitis C virus core, NS3, NS4B and NS5A are the major immunogenic proteins in humoral immunity in chronic HCV infection. Virology J 2009; 6:84-96

Lefrere J, Guiramand S, Lefrere F et al. Full or partial seroconversion in patients infected by hepatitis C virus. J Infect Dis 1997; Vol 175: 316-322

Courouce A, Le Marrec N, Girault A, Ducamp S, Simon N. Anti-hepatitis C virus (anti-HCV) seroconversion in patients undergoing hemodialysis: comparison of second- and third-generation anti-HCV assays. Transfusion 1994; Vol 34; 790-795

Laperche S. Simultaneous detection of anti-HCV Ab and HCV core antigen. Roche infectious diseases symposium, Barselona, Spain, 2009, 8 Oct.

Riabinina S, Baranova E, Sharipova I, Susekina M, Puzyrev V, Obriadina A, Burkov A, Ulanova T. Evaluation of diagnostic efficiency of the recombinant protein modeling immunodominant epitope V3 of envelope gp120 for immunoenzyme detection for HIV-1 infection antibodies. Mol Gen Mikrobiol Virusol 2007; 3:33-36

Baranova E, Puzyrev V, Vankova O, Pimenov V, Burkov A, Obriadina A, Ulanova T. Comparison of the diagnostic value of recombinant antigens and synthetic peptides that mimic the immunogenic epitopes of the envelop protein gp41 in the enzyme immunodetection of HIV-1 antibodies. Vopr Virusol. 2006 May-June; 51(3):46-48

Yeh C-T, Han C-M, Lo S-Y, Ou J-H, Fan K-D, Sheen I-S, Chu C-M, Liaw Y-F. Early detection of anti-HCc antibody in acute hepatitis C virus (HCV) by western blot (immunoblot) using a recombinant HCV core protein fragment. J Clin Microbiol 1994; September: 2235-2241

Lin S, Arcangel P, Medina-Selby A, Coit D, Ng P, Nguyen S, McCoin C, Gyenes A, Hu C, Tandeske L, Phelps B, Chien D. Design of novel conformational and genotype-specific antigens for improving sensitivity of immunoassays for hepatitis C virus-specific antibodies. J Clin Microbiol 2005; August: 3917-3924

Evaluation of Murex HCV Ag/Ab Combination. MiDAS, London 2007:1-18

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. These patents and publications are incorporated herein by reference to the same extent as if each individual application or publication was specifically and individually stated herein as incorporated herein by reference for the entirety of their teaching.

The foregoing description is illustrative of particular embodiments of the invention, but is not meant to be a limitation upon the practice thereof.

The invention claimed is:

1. A detection agent for the detection of an antibody directed to HCV core protein,
   wherein the detection agent is capable of being specifically bound by the antibody directed to HCV core protein;
   wherein the detection agent comprises a peptide comprising:
      a first epitope region consisting of SEQ ID NO: 2;
      a second epitope region consisting of SEQ ID NO:3 or SEQ ID NO: 3 excluding the C-terminal residue; and
      a linker positioned between the first epitope region and the second epitope region, the linker excluding any portion of SEQ ID NO: 1;
   and wherein the detection agent excludes contiguous amino acids 1-13, contiguous amino acids 32-49 and contiguous amino acids 100-120 of SEQ ID NO: 1.

2. The detection agent of claim 1, wherein the linker is an amino acid or an amino acid sequence of 2 to 50 amino acids.

3. The detection agent of claim 2, wherein the linker comprises 5 or more amino acids.

4. The detection agent of claim 3, wherein the linker comprises SEQ ID NO: 4.

5. A process of detecting a presence or absence of HCV in a biological sample, comprising:
- contacting the biological sample with a detection agent capable of being specifically bound by an antibody directed to HCV core protein and comprising a peptide comprising a first epitope region consisting of SEQ ID NO: 2, a second epitope region consisting of SEQ ID NO:3 or SEQ ID NO: 3 excluding the C-terminal residue and a linker positioned between the first epitope region and the second epitope region, the linker excluding any portion of SEQ ID NO: 1, wherein the detection agent excludes contiguous amino acids 1-13, contiguous amino acids 32-49 and contiguous amino acids 100-120 of SEQ ID NO: 1;
- contacting the biological sample with a detection antibody, wherein the detection antibody is polyclonal, capable of specifically binding to an epitope within HCV core protein and does not bind specifically to the detection agent;
- detecting a presence or absence of the antibody directed to the HCV core protein in the biological sample, wherein detection of the specific binding of the detection agent to the antibody directed to HCV core protein in the biological sample indicates the presence of HCV in the biological sample; and
- detecting a presence or absence of HCV core protein in the biological sample, wherein detection of specific binding of the detection antibody to HCV core protein in the biological sample indicates the presence of HCV in the biological sample.

6. The process of claim 5, wherein the detection antibody is generated against an immunogen excluding the first epitope region and the second epitope region.

7. The process of claim 5, wherein the detection agent is a peptide consisting of SEQ ID NO: 2 and SEQ ID NO:3, connected by a linker.

8. The process of claim 5, wherein the biological sample is selected from the group consisting of blood, plasma and serum.

9. A kit for detection of HCV in a subject comprising:
- the detection agent of claim 1; and
- a pharmaceutically acceptable carrier.

10. A kit for detection of HCV in a subject, comprising:
- the detection agent of claim 1; and
- a detection antibody, wherein the detection antibody is polyclonal, capable of specifically binding to an epitope within HCV core protein and does not bind specifically to the detection agent.

11. The kit of claim 10, wherein the detection antibody is generated against an immunogen excluding the first epitope region and the second epitope region.

12. The kit of claim 10, wherein the immunogen comprises one or more of contiguous amino acids 1-13, contiguous amino acids 32-49 and contiguous amino acids 91-120 of SEQ ID NO:1.

13. The process of claim 6, wherein the immunogen comprises one or more of contiguous amino acids 1-13, contiguous amino acids 32-49 and contiguous amino acids 91-120 of SEQ ID NO:1.

14. The detection agent of claim 1, wherein the detection agent is a peptide consisting of the first epitope region and the second epitope region connected by a linker.

15. The detection agent of claim 1, wherein the peptide has 70 or fewer amino acids, excluding the linker.

* * * * *